United States Patent
Amelard et al.

(10) Patent No.: US 10,709,342 B2
(45) Date of Patent: Jul. 14, 2020

(54) SYSTEM AND METHOD FOR SPATIAL CARDIOVASCULAR MONITORING

(71) Applicants: Robert Andre Amelard, Waterloo (CA); Alexander Sheung Lai Wong, Waterloo (CA)

(72) Inventors: Robert Andre Amelard, Waterloo (CA); Alexander Sheung Lai Wong, Waterloo (CA)

( * ) Notice: Subject to any disclaimer, the term of this patent is extended or adjusted under 35 U.S.C. 154(b) by 410 days.

(21) Appl. No.: 15/387,365

(22) Filed: Dec. 21, 2016

(65) Prior Publication Data
US 2017/0172434 A1    Jun. 22, 2017

Related U.S. Application Data

(60) Provisional application No. 62/270,409, filed on Dec. 21, 2015.

(51) Int. Cl.
*A61B 5/024*     (2006.01)
*A61B 5/00*      (2006.01)
(Continued)

(52) U.S. Cl.
CPC ........ *A61B 5/02416* (2013.01); *A61B 5/0077* (2013.01); *A61B 5/02427* (2013.01);
(Continued)

(58) Field of Classification Search
CPC ......... A61B 5/00; A61B 5/026; A61B 5/0295; A61B 5/0075; A61B 5/0261;
(Continued)

(56) References Cited

U.S. PATENT DOCUMENTS

2017/0079530 A1*  3/2017  DiMaio ............... A61B 5/0075

* cited by examiner

*Primary Examiner* — Jon Eric C Morales
(74) *Attorney, Agent, or Firm* — Tai W. Nahm; Miller Thomson LLP

(57) ABSTRACT

There is disclosed a system and method for measuring arterial and venous blood pulse waveforms (BPWs) of a subject utilizing photoplethysmography (PPG). In an embodiment, the system and method comprises: providing a plurality of virtual sensors positioned to cover a desired field-of-view of the subject, each virtual sensor adapted to detect and measure a BPW signal from an area of the subject's body and provide a BPW signal output; processing the BPW signal outputs of the plurality of virtual sensors to compare the BPWs at multiple areas of the subject's body to perform spatial perfusion analysis; and displaying at least one aggregate output based on the spatial perfusion analysis. At least one aggregate output may include a visualization of one or more perfusion patterns overlaid on a photographic image of the subject, and aggregate statistics including subject heart rate and breathing rate. The system and method may use a signal from one of the virtual sensors as a reference waveform for cardiovascular monitoring in the generation of parametric maps for assessing BPW characteristics at various parts of the body simultaneously. The system and method may also include a contact photoplethysmography (PPG) sensor, which is connected to the DSP and provides a BPW as a reference waveform for improved cardiovascular monitoring in the generation of parametric maps for assessing BPW characteristics at various parts of the body simultaneously.

24 Claims, 11 Drawing Sheets

(51) Int. Cl.
*A61H 31/00* (2006.01)
*A61B 5/1455* (2006.01)

(52) U.S. Cl.
CPC .......... *A61B 5/4848* (2013.01); *A61B 5/7278* (2013.01); *A61B 5/742* (2013.01); *A61B 5/743* (2013.01); *A61H 31/005* (2013.01); *A61B 5/14552* (2013.01); *A61B 2562/046* (2013.01)

(58) Field of Classification Search
CPC ..... A61B 5/0064; A61B 5/445; A61B 5/7264; A61B 5/0205; A61B 5/4875; G16H 30/40; G16H 50/20; G06F 19/00; Y02A 90/26
See application file for complete search history.

SYSTEM AND METHOD FOR SPATIAL CARDIOVASCULAR MONITORING

FIELD OF THE INVENTION

The present disclosure relates generally to the field of cardiovascular imaging systems.

BACKGROUND

Photoplethysmography (PPG) is a technique that has been used since the 1930s for assessing cardiovascular function [1]. Its use has become widespread in hospitals due to its relatively low cost and ease of use. In its simplest form, it consists of two primary components: a light source and a light detector. The light source illuminates the tissue with constant optical power, and the light detector detects the amount of light transmitted through the tissue. The light output fluctuates with each blood pulse resulting from a cardiac cycle, resulting in the extraction of a blood pulse waveform or BPW.

PPG devices rely on the properties of light-tissue interaction. Light that penetrates the surface of the skin interacts with the underlying tissues in two primary ways: scattering and absorption. When perfectly reflected and scattered by a molecule, a photon of light changes direction and possibly polarization, but retains its original energy level. Alternatively, a photon of light may be absorbed by certain types of molecules called "chromophores" (such as hemoglobin and melanin), resulting in a fewer number of photons being re-emitted. Chromophores are thus characterized by spectral absorption profiles called "extinction coefficients". As an illustrative example, when the heart enters systole during a cardiac cycle, blood is pumped through the arterial system, causing a transient increase in blood volume at the traveling area of the pulse. This change in blood volume modifies the temporal illumination profile passing through the vasculature, resulting in a BPW that is displayed on PPG monitors.

The first known PPG imaging (PPGI) system was proposed in 2002 by M. Hulsbusch and V. Blazek [2] using a cooled near infrared CCD camera to assess wound healing. The authors used a wavelet transform to show noisy pulsatile components around an ulcer wound. They further demonstrated preliminary results using transmittance through a fingertip. However, their setup was expensive, did not produce real-time analysis, and produced noisy BPW signals.

In 2005, Wieringa et al. published a PPGI system and method for extracting blood pulse oxygen levels [3]. Their PPGI system was controlled and synchronized to an ECG and finger cuff using a footswitch and in-frame background light. They used a combination of a modified camera (since obsolete), and 300 LED ring light of wavelength 660 nm, 810 nm, and 940 nm. Regions of 10×10 pixels were averaged to reduce noise. Their low frame rates limited the real-time applicability. This experiment, like many others, was assessed in darkroom settings, void of ambient light. The "relative spectral power" map was calculated with a hardcoded heart rate, and limited to the hand/wrist region of a subject.

In 2007, Humphreys et al. published a PPGI system that extended on Wieringa's [4]. An 8×8 LED grid separate from the camera was used to illuminate the skin. Synchronization was done using electronic switches. Like Wieringa's system, a background light was used for synchronization. However, the results were restricted to forearm measurements of heart rate and blood oxygen metrics only.

Since these initial studies, there have been other PPGI systems proposed. However, most of these systems are restricted to measuring heart rate [15] over either the hand/wrist area [5] or the face [6] [7] [8], and many rely on limited methods for reducing noise, such as windowed averaging [9] [10]. Moreover, many are validated only in darkroom settings [11] [5] [7], which limit their applicability in real-world, clinical environments where darkroom settings may be difficult to establish.

More recently, Kamshilin et al. [12] used two identical green LEDs and a camera along with a synthetic BPW to construct a visualization of pixel-by-pixel perfusion and pulsing. However, once again, their findings were restricted to constrained environments of hand/wrist imaging, and the method required prerequisite knowledge of the heart rate, and could not detect heart rate automatically. What is needed is an improved system and method for spatial cardiovascular monitoring that overcomes at least some of the above described limitations in the prior art.

SUMMARY

The present disclosure describes a system and method for detecting, measuring and displaying arterial and venous blood pulse waveforms (BPWs) at various parts of the body simultaneously through one or more virtual sensors. In an embodiment, the virtual sensors may comprise an array of optical sensors which may be positioned to cover a desired field-of-view of a subject to capture illumination fluctuations on the subject. Each virtual sensor may be adapted to detect and measure a BPW signal from an area of the subject's body. The output of one or more virtual sensors is processed using a digital signal processing unit (DSP) to extract the BPW from the noise, and to process multiple BPW signals simultaneously from various parts of the subject's body, thereby allowing a comparison of BPWs at multiple locations and analysis of spatial perfusion. This may provide a more complete picture of the status of the subject throughout the body, and aid in the analysis of the subject's condition.

Advantageously, the present system and method provides a solution for assessing the temporal BPW of a subject at various locations of the patient subject's body using virtual sensors, illumination, and advanced DSP algorithms for signal extraction. The system and method also permit the generation of derivative visualizations (e.g., parametric maps, flow overlay, etc.) for assessing BPW characteristics at various parts of the body simultaneously. Furthermore, the system and method also permit the inclusion of a contact photoplethysmography (PPG) sensor, which is connected to the DSP and provides a reference blood pulse waveform as a reference waveform for improved cardiovascular monitoring capabilities.

Figure 1:
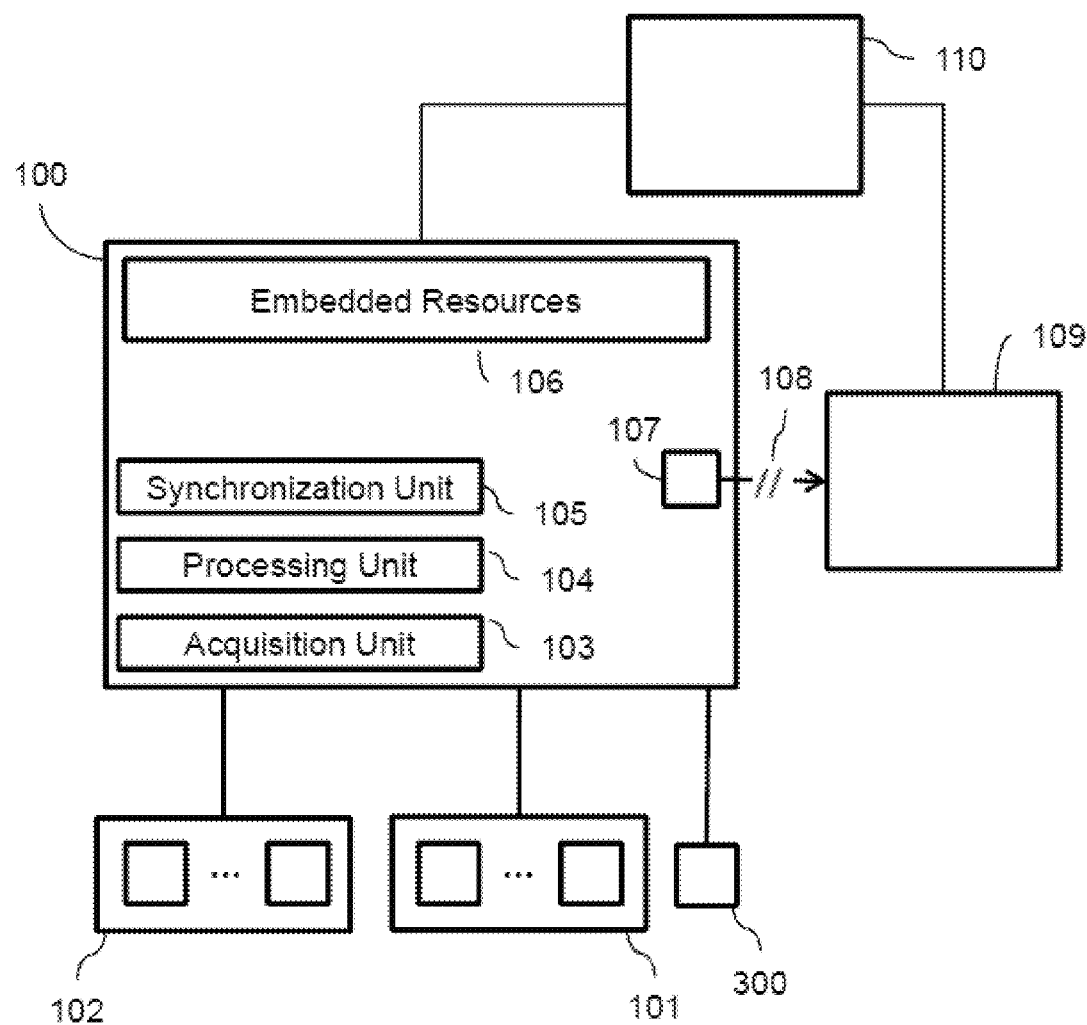
FIG. 1 shows a block diagram representation of the system in accordance with an embodiment.

In the drawings, various embodiments are illustrated by way of example. It is to be expressly understood that the description and drawings are only for the purpose of illustration and as an aid to understanding, and are not intended as describing the accurate performance and behavior of the embodiments and a definition of the limits of the invention.

DETAILED DESCRIPTION

As noted above, the present disclosure relates generally to the field of cardiovascular imaging systems, and more particularly to a system and method for detecting and measuring blood pulse waveforms (BPWs) at various parts of a subject's body simultaneously through one or more virtual sensors.

While various prior art photoplethysmography (PPG) imaging systems and methods have been proposed as summarized in the Background section above, as noted, they have various drawbacks which limit their applicability in certain applications. As will be detailed below, the present system and method is designed to provide a solution which addresses at least some of the drawbacks in the prior art to improve analysis of a subject's condition.

In an aspect, the present system and method utilizes one or more virtual sensors comprising one or more optical sensor arrays to extract BPWs from multiple locations on a subject's body simultaneously. These locations are not limited to the face, hand or forearm as in some prior art, but may be any part of the subject's body that is of interest. This type of spatial analysis is important for diagnostic purposes. For example, peripheral arterial disease is characterized by an increase in vascular resistance in peripheral areas of the body, most commonly the legs. Arterial stiffness is characterized by the stiffening of the arteries, usually over age. Stiff arteries often lead to complications, such as high blood pressure, and can be detected by evaluating the pulse transit timing between major arterial channels.

Spatial perfusion analysis is important for assessing the viability of a large area of tissue, due in part to the supply of blood to the tissue. This is important in, for example, breast reconstruction with flap surgery. Blood pressure can be estimated by evaluating the BPW at various locations simultaneously. Assessing the BPW at various parts of the body can help detect the aforementioned phenomena.

Various embodiments of the present system and method will now be described in more detail with reference to the figures.

FIG. 1 depicts a block diagram of the system in accordance with an illustrative embodiment. An array of BPW sensors 101 provides signal input into a central system unit 100. This central system unit 100 can be, for example, a generic computing device (see FIG. 11 below) or an embedded system. An acquisition unit 103 acquires the BPW data. The BPW data is processed by a processing unit 104, explained in more detail below. A synchronization unit 105 may synchronize illumination and sensor components required to illuminate a subject and collect data. These various units may utilize embedded resources 106, such as a central processing unit (CPU), a digital signal processing unit (DSP), and graphics processing units (GPU). An aggregate output, described in detail below, may be relayed to a visualization unit 109 through a communication unit 107 via a communication layer 108, such as over a wireless network, wired network, or communication bus. A user interface unit 110 is connected to both the central system unit 100 and visualization unit 109 to provide user interaction. In some embodiments, a reference BPW sensor 300 may be connected to the system to provide the reference signal.

In operation, given expected light fluctuations across an area of interest, each location of a subject's body is covered by a virtual sensor and is treated independently. Thus, multiple BPW readings are acquired through multiple virtual sensors.

The one or more virtual sensors may be, for example, a combination of one or more optical sensors which can be directed to or positioned towards any part on a subject's body to obtain a BPW measurement. The one or more virtual sensors may be arranged in virtual groupings of individual pixels of a large array of optical sensors, such as a digital camera sensor, for example. Thus, a single digital camera sensor may contain multiple virtual sensors. Alternatively, multiple digital camera sensors may be positioned at multiple locations to cover a desired field-of-view, and each digital camera sensor may contain one or more virtual sensors. Examples of optical sensor arrays may include a complementary metal-oxide-semiconductor (CMOS) sensor, charge-coupled device (CCD) sensor, contact patches with embedded sensors, and distributed individual optical sensors, such as photodetectors.

Furthermore, the present system and method may perform region of interest aggregation using digital signal processing (DSP). Advanced DSP is utilized to process multiple BPW signals simultaneously from various parts of the subject to enable generation of aggregate parametric maps for assessing BPW characteristics at various parts of the body simultaneously. Advantageously, the present system and method allows a more complete picture of a subject's BPW pattern throughout the body to provide better information to determine the status of the subject.

Furthermore, the present system and method may perform the generation of parametric maps for assessing BPW characteristics at various parts of the body simultaneously. These parametric maps may be used to assess temporal pulsatility characteristics and identify areas with strong or weak pulsatile flow.

Furthermore, the present system and method may also permit the inclusion of a contact photoplethysmography (PPG) sensor, which is connected to a DSP and provides a BPW as a reference waveform for improved cardiovascular monitoring capabilities.

Figure 2:
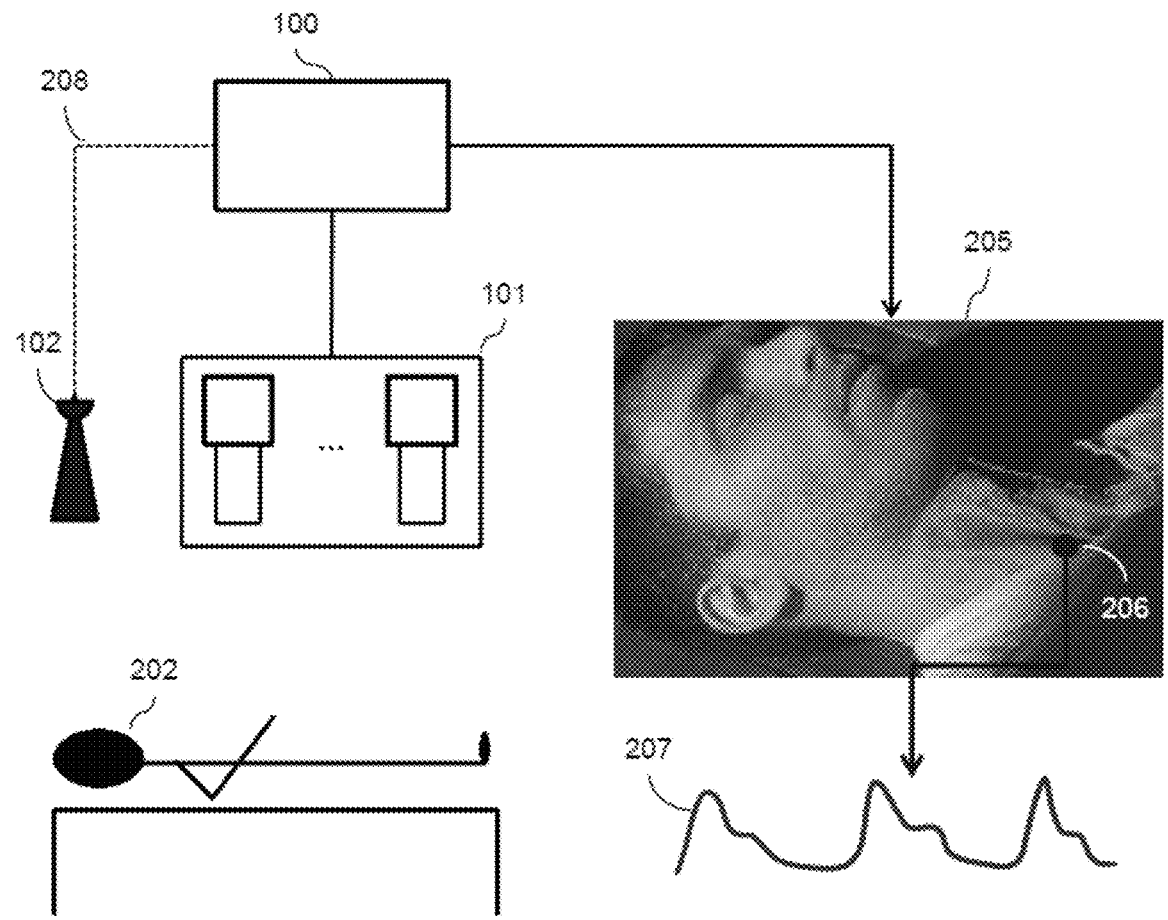
FIG. 2 shows a graphical example of the system and method in reflectance mode in accordance with an embodiment.

Referring to FIG. 2, shown is a schematic illustration of the system in reflectance mode in accordance with an embodiment. As shown, an illumination source 102 and one or more BPW sensors 101 are positioned at any part of a subject's body 202 that is of interest. For example, this may include the head, neck and upper chest, or it could include the entire body of the subject. Examples of a subject include patients in a clinical environment, individuals at home, older adults in a retirement or long-term care home, or an infant at home or in a neonatal intensive care unit. The illumination source 102 is optionally connected to the central system unit 100 for synchronization with the BPW sensors 101. The data collected by the BPW sensors 101 is processed into an aggregate visualization 205, where the BPW at each virtual sensor 206 can be analyzed 207. As shown in FIG. 2, the visualization of the BPW data can be overlaid on top of a photographic image of the subject to clearly show the location from which the BPW data was collected.

In an embodiment, the BPW sensors 101 capture light from a subject's body. Digital signal processing (DSP) is applied to the resulting frames to generate a virtual sensor at each part of the body, whereby BPWs can be extracted. A virtual sensor is composed of groups of one or more optical sensors. Further analysis can be performed, such as pulse transit timing, and pulse amplitude analysis. Parametric maps, such as signal-to-noise ratio (SNR) and entropy, can be generated. Furthermore, the signal from one of the virtual sensors can be used as a reference waveform, which enables the generation of parametric maps comparing the virtual sensor outputs to this reference waveform, such as signal-to-noise ratio and relative spectral peak power.

In an illustrative embodiment, an optical sensor array detects light fluctuation resulting from light that has entered and passed through subject's skin and/or tissue. This light will have undergone absorption and perhaps scattering phenomena due to molecules in the skin and tissues such as oxyhemoglobin, deoxyhemoglobin, and melanin. The optical sensor data is sent to a DSP controller that analyzes the data and extracts the BPW at each virtual sensor location.

In another illustrative embodiment, a camera and light source is operatively connected to a computer to detect the BPW at points on the surface of the subject's skin. In these non-contact implementations, neither the camera nor the light source are touching the subject's skin. In an embodiment, pixels forming a large array of optical sensors are grouped (e.g., using averaging) to form "virtual sensors" covering particular locations on the subject's skin.

Denoting a virtual sensor's intensity value at location (x,y) over time t as I(x,y,t), the virtual sensor's output is calculated using the inverse law relationship of reflectance and absorption from Beer-Lambert law. The Beer-Lambert law shows that the attenuation of light follows an exponential decay as it passes through a homogeneous light-absorbing medium:

$$T = \frac{I}{I_0} = e^{-\epsilon l c}$$

where T is transmittance, $I_0$ is incident light, I is transmitted light, $\epsilon$ is the tabulated molar extinction coefficient for the light-absorbing medium, l is the photon path length, and c is the concentration of the medium. The spatio-temporal transmittance can be written as a function of time:

$$T(x, y, t) = \frac{I(x, y, t)}{I_0(x, y)} = e^{-\epsilon l(x,y,t) \cdot c(x,y,t)}$$

The standard measurement signal for BPW analysis is absorption (which is directly correlated with blood volume), which exhibits an inverse logarithm law relationship with transmittance:

$$BPW(x, y, t) = \log\left(\frac{I_0(x, y)}{I(x, y, t)}\right)$$

In some embodiments, the light source and BPW sensors are on the same side of the tissue, in "reflectance mode", as shown by way of example in FIG. 2. The optical sensor array detects light that has entered the tissue and subsequently scattered back toward the surface while undergoing photonic absorption events.

Figure 3:
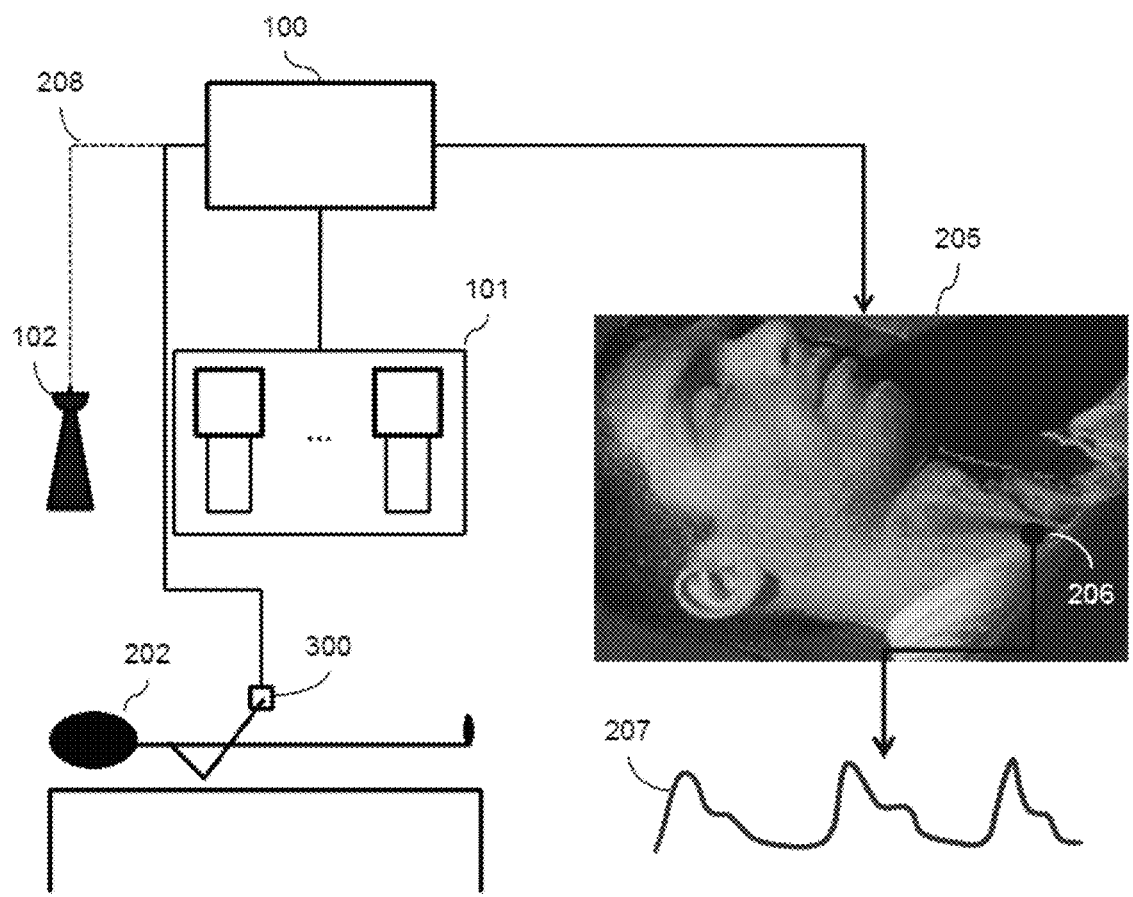
FIG. 3 shows the system and method in reflectance mode again, but this time with the inclusion of a contact photoplethysmography (PPG) sensor, which is connected to the DSP in accordance with an embodiment.

Now referring to FIG. 3, the system is once again shown in reflectance mode, but this time with the inclusion of a contact photoplethysmography (PPG) sensor 300 on the subject, which is connected to the central system unit 100. In this embodiment, the contact PPG sensor provides a reference BPW, which enables the generation of parametric maps comparing the virtual sensor outputs to the contact PPG signal as the reference signal, such as signal-to-noise ratio and relative spectral peak power.

Figure 4:
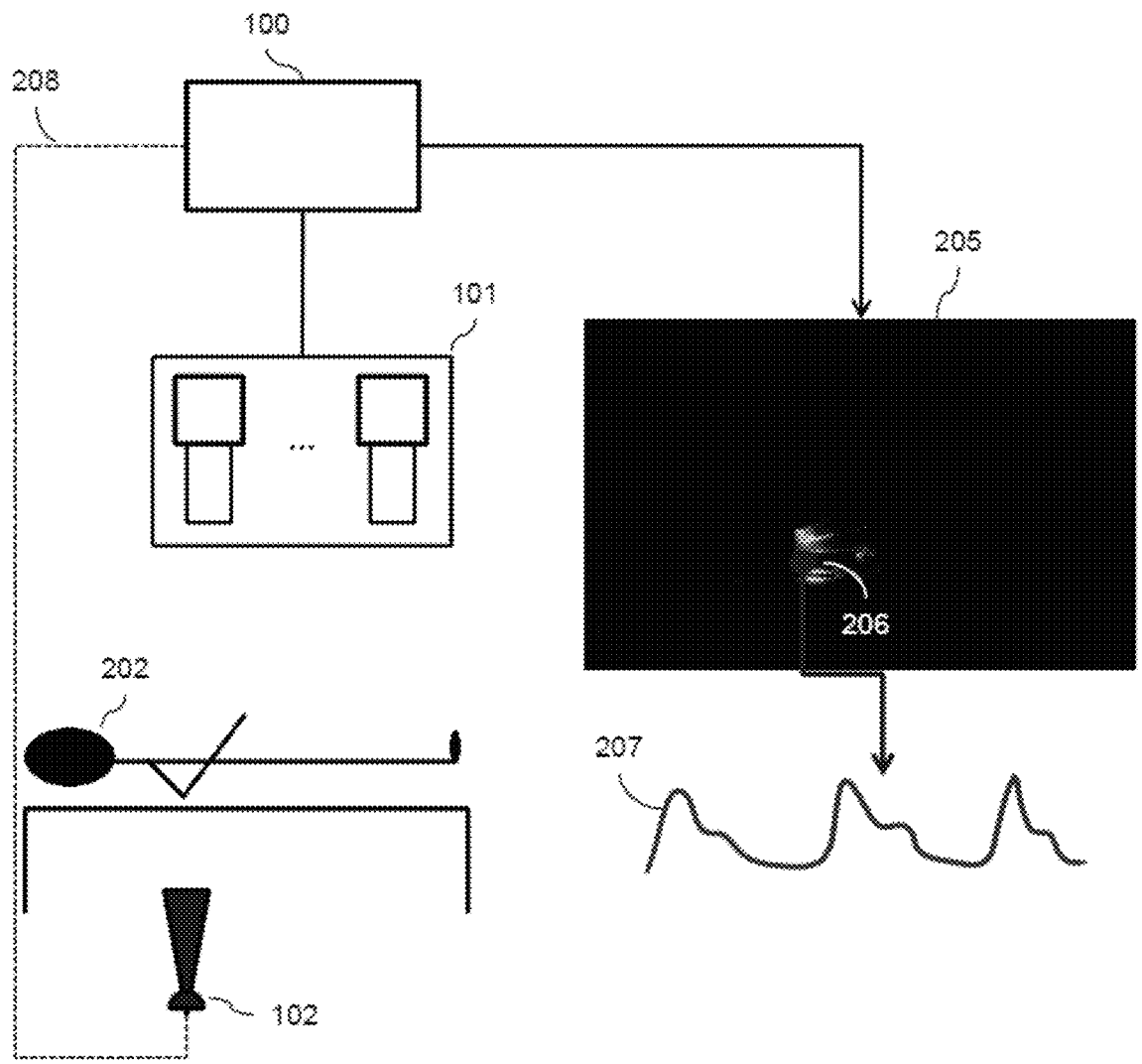
FIG. 4 shows the system and method in transmittance mode, where the light and sensor are placed on either side of the tissue under analysis in accordance with an embodiment.

In an alternative embodiment, as shown in FIG. 4, the system and method may operate in transmittance mode, where the illumination source 102 and BPW sensors 101 surround the tissue of a subject's body 202 under analysis. The light transmitted through the tissue is analyzed in a similar way as in reflectance mode, producing a series of BPWs across multiple locations. Transmittance mode systems are more hygienic than contact-based sensors, such as finger PPGs, are able to compensate for peripheral motion, and enable spatial analysis.

In some implementations, the light sources that can be used include, but are not limited to, incandescent light sources (such as halogen light sources), light emitting diode (LED) light sources, fluorescent light sources, and xenon strobe light sources. In other implementations, the light sources can be the Sun, or ambient lighting, and may not be connected to the electronics as shown by the dashed line 208 in FIGS. 2-4.

In an embodiment, the BPW sensors 101 export light data to a DSP unit. The DSP processes the input to generate BPWs from the virtual sensors, and may compute cardiovascular parameters such as heart rate, interbeat intervals, respiratory rate, and heart rate variability. The computer stores the data in memory. The computer displays the results in a graphical user interface onto an I/O device that is attached physically or through a network connection, such as a monitor or a smartphone. In another implementation, the DSP is performed using on-board embedded computing.

Figure 5:
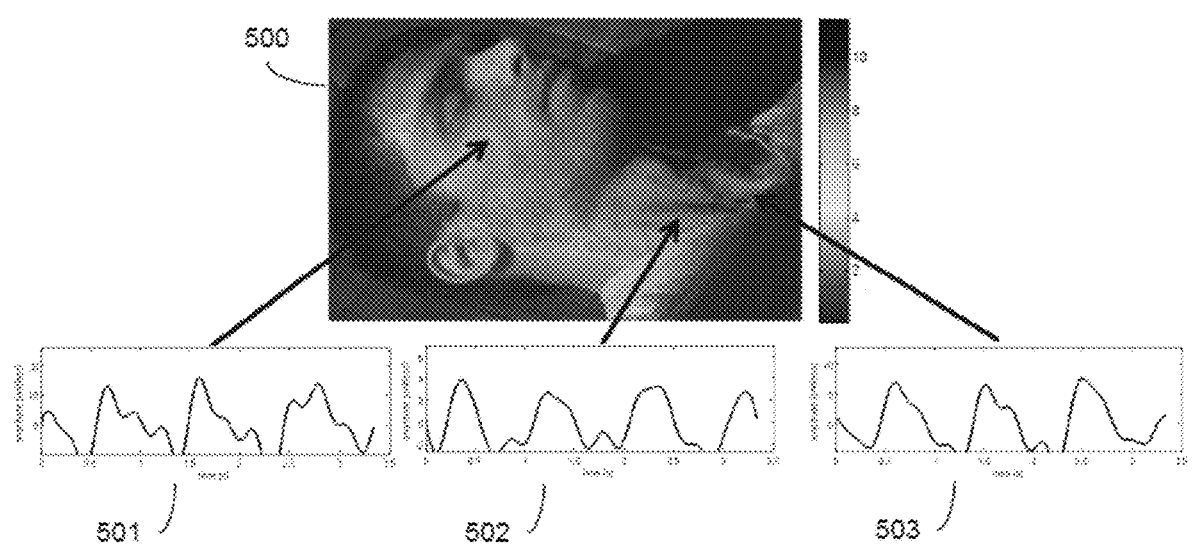
FIG. 5 shows an example visual output of the system and method in accordance with an embodiment.
Figure 6A:
FIGS. 6A-6D show different examples of parametric maps that may be generated using the system and method in accordance with an embodiment.
Figure 6B:
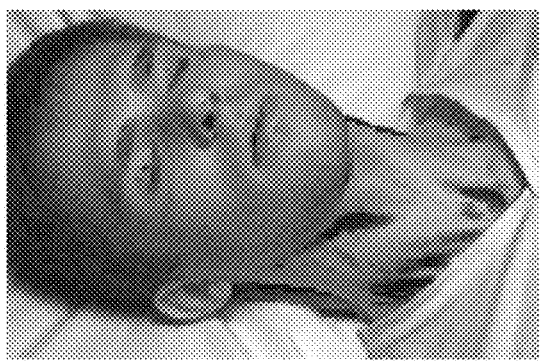
Figure 6C:
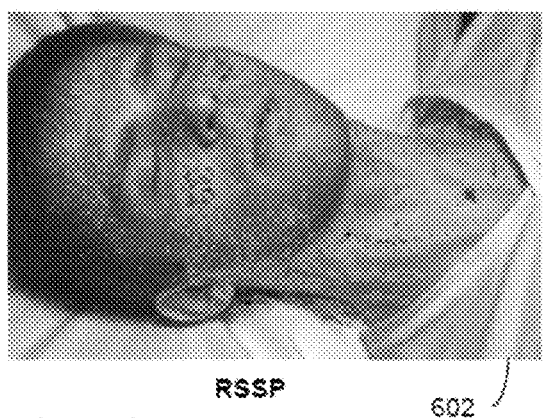
Figure 6D:

Now referring to FIG. 5, shown is an example output of the system. In this illustrative example, an SNR parametric map visualization 500 is generated to show the areas with strong BPWs. Using a color screen, different parts of the subject may be shown in different colors to show BPW intensity (e.g. red indicates strong BPW, blue indicates weak or no BPW). BPWs from the system are shown in three locations 501, 502, 503 and may be compared to the BPW from a contact PPG sensor 300, which is used as a reference signal. Note that in some implementations, the BPW from one of the virtual sensors can be used as a reference signal instead of the BPW from a contact PPG sensor 300.

In some implementations, the spatial location of the skin can be tracked if the camera and/or user are moving. Tracking and movement compensation can be performed through DSP methods that employ object or landmark tracking over frames. Thus, the coordinates of I*(x,y,t) are corrected to the area of interest. In particular, given movement-induced transformation Y, the motion-corrected frame is computed as:

$$f(x,y,t)=Y^{-1}(g(x,y,t)) \quad \quad 5$$

where g(x,y,t) is the captured frame, and f(x,y,t) is the motion-corrected frame.

In some implementations, the system includes a contact PPG sensor 300 that is placed on the user and provides a BPW as a reference waveform for improved cardiovascular monitoring capabilities. In other implementations, the BPW from one of the virtual sensors may be used as a reference waveform instead of the BPW.

In some implementations, the light source and BPW sensors are positioned on opposite sides of a part of the subject's body, such as a finger. The light undergoes similar light-tissue interactions, and the fluctuations of light incident on the sensors are recorded and processed to elucidate the BPW.

Human movement results in another type of noise. The incident on the skin decreases as the skin moves further away, and increases as the skin moves closer. To compensate for these fluctuations in illumination, a detrending method is used. One example of a detrending method estimates a slow trend over time, and removes this trend from the original data. Mathematically, the BPW is modeled as the sum of two latent signals:

$$BPW(x,y,t)=BPW_{true}(x,y,t)+BPW_{trend}(x,y,t)$$

Given that BPW(x,y,t) is measured, $BPW_{true}(x,y,t)$ can be solved by estimating $BPW_{trend}(x,y,t)$ assuming a linear model, subtracting it from the original signal, and solving using regularized least squares, which provides the following estimate of the true detrended signal (in matrix form) [13]:

$$\widehat{BPW}_{true}=(I+\lambda^2 D_2^T D_2)^{-1}A$$

where I is the identity matrix, λ is a relative weighting term, and $D_2$ is the discrete approximation of the second derivative. The resulting $\widehat{BPW}_{true}(x,y,t)$ is a spatial-spectral data cube, containing BPWs for each location.

FIGS. 6A-6D show different examples of aggregate parametric maps that may be generated using the system. Here, signal-to-noise ratio 600, entropy 601, relative spectral peak power 602, and Pearson's linear correlation coefficient 603 are shown in FIGS. 6A-6D, respectively. As shown in FIGS. 6A-6D, each type of aggregate parametric map can be overlaid on a photographic image of the subject, such that the exact location from which the data was collected can be shown. Different colors may be used to identify different regions of a subject's body covered by each type of parametric map. These different types of parametric maps as illustrated in FIGS. 6A-6D may be used to identify and elucidate different characteristics of blood flow to assist in analysis of a subject's condition.

In one embodiment of the system, a camera system is used with a finger PPG to identify the strength of the BPW at all locations of the skin. The PPG is treated as the reference signal. The computational backend calculates the signal-to-noise ratio (SNR) of each virtual sensor to determine a BPW strength map. Mathematically, given the spectral magnitudes of the camera at location (x,y) (M) and PPG (M*), calculated for example by the Fourier transform, the SNR is calculated as:

$$SNR(M, M^*) = 10\log_{10} \frac{\sum_i S_i^2}{\sum_i N_i^2}$$

for each frequency bin i, where $$S = \frac{M^*}{\sum_j M_j^*}$$

$$N = \frac{M}{\sum_j M_j} - S$$

Another metric that can be used is the relative spectral peak power:

$$RSSP(M, M^*) = \frac{M_{hr}^2}{\sum_{i \in \{1,\ldots,n\}\setminus\{hr-1,hr,hr+1\}} M_{hr}^2}$$

where hr is the frequency index representing the heart rate, which can be found through peak analysis on M*.

Another metric that can be used is Pearson's linear correlation coefficient (PLCC):

$$PLCC(b^{(1)}, b^{(2)}) = \frac{\sum_i (b_i^{(1)} - \overline{b^{(1)}})(b_i^{(2)} - \overline{b^{(2)}})}{\sqrt{\sum_i (b_i^{(1)} - \overline{b^{(1)}})^2} \sqrt{\sum_i (b_i^{(2)} - \overline{b^{(2)}})^2}}$$

where $b^{(1)}$, $b^{(2)}$ are two BPWs.

In another embodiment of the system, a camera system (from which virtual sensors are obtained) is used without a contact PPG sensor to identify the strength of the BPW at all locations of the skin. The BPW of one of the virtual sensors is treated as the reference signal. The DSP backend calculates the SNR, RSSP, or PLCC of each virtual sensor relative to the reference signal (which is the BPW of one of the virtual sensors) to determine a BPW strength map.

In yet another embodiment of the system, a BPW strength map is generated without the use of a finger PPG cuff. Instead, an approximation of SNR is computed. For example, entropy can be used to approximate SNR, since it is expected that a high SNR signal will have low entropy. In particular spectral entropy for the signal at location (x,y) can be calculated as:

$$H(x, y) = -\sum_i P_i \log_2 P_i$$

where $P_i$ is the spectral power of the signal at location (x,y) for frequency i. This entropy can be thresholded to only consider signals that are cleanly within physiologically valid heart rates (e.g., 30-250 bpm).

These point-based metrics are used to generate parametric maps based on the data cube, where each point in the map contains a value. These can be used to assess blood perfusion across an area. For example, an SNR, RSSP, PLCC, or entropy parametric map can help identify areas with strong pulsatility at that location. For example, a phase correlation map can help identify the relative phase, or pulse timing, at different parts of the body.

In one embodiment of the system, enhanced BPWs can be extracted from a video. In this embodiment, a metric can be used to weight individual locations' signals based on their signal power. This can be expressed as a Bayesian least squares formulation:

$$\hat{z} = \operatorname{argmin}_{\hat{z}} \{E[(\hat{z}-z)^T(\hat{z}-z) \mid X]\}$$
$$= \operatorname{argmin}_{\hat{z}} \int (\hat{z}-z)^T(\hat{z}-z) P(z \mid X) dz$$

where $P(z|X)$ is the posterior probability of z being the BPW signal given the measurements X. The optimal solution is found by setting the derivate to 0, simplifying the equation to:

$$\hat{z} = \int z P(z|X) dz$$

In order to solve this equation, the posterior distribution must be modeled. This can be done, for example, using a weighted average approach:

$$P(z \mid X) = \prod_i p_i x_i$$
$$p_i = \frac{w_i}{\sum_j w_j}$$

In some implementations, a spatial-spectral weighting scheme is used to identify the signals that have high signal fidelity (low entropy) and do not occur at a boundary. The spectral weight can be defined, for example, as:

$$w_i^e = \begin{cases} \exp\left(-\frac{(H_i^*)^2}{\alpha_1}\right), & \text{if the maximum peak is physiologically valid} \\ 0, & \text{otherwise} \end{cases}$$

where $H_i^*$ is the normalized spectral entropy, and $\alpha_1$ is a tuning parameter. The spatial weight can be defined, for example, as:

$$w_i^s = \exp\left(-\frac{G_i^2}{\alpha_2}\right)$$

where $G_i^2$ is the squared discrete gradient across the image, and $\alpha_2$ is a tuning parameter. Then, the posterior distribution can be defined using:

$$w_i = w_i^e w_i^s$$

The result is an enhanced BPW data cube for a subset location. For example, the spatial-spectral enhancement can be applied to extract a more robust BPW at each virtual sensor. Other weights can be used in the same framework. This BPW can be analyzed to calculate cardiac measurements, such as heart rate, heart rate variability, interbeat interval, respiratory rate, and identify arrhythmias. Respiratory rate can be extracted by analyzing the interbeat intervals, since heart rate is mediated by the change in lung volume. Blood oxygen saturation can be extracted using 2 or more wavelengths on either side of oxy and deoxyhemoglobin's isosbestic point, where the two chromophore's absorption ability crosses over (e.g., there is one at 805 nm) and measuring the difference in absorption relative to a calibrated reflectance standard. For example, given two wavelengths $\lambda_1$, $\lambda_2$, the modulation ratio can be calculated by:

$$M = \frac{AC_{rms}^{(\lambda_1)} / DC^{(\lambda_1)}}{AC_{rms}^{(\lambda_2)} / DC^{(\lambda_2)}}$$

where $AC_{rms}$ is the pulsatile signal component, and DC is the steady state signal component. M could also be calculated solely using the AC component:

$$M = \frac{AC_{rms}^{(\lambda_1)}}{AC_{rms}^{(\lambda_2)}}$$

Then a calibration procedure can be used to produce a calibrated oxygen saturation model:

$$S_pO_2 = f(M|S)$$

where $f(\cdot|S)$ is a calibrated model given the known S, which is the true $S_pO_2$ value. A linear model could be expressed as:

$$S_pO_2 = a - bM$$

where a, b are calibration parameters acquired in a controlled calibration setting knowing the true value of $S_pO_2$.

Figure 7:
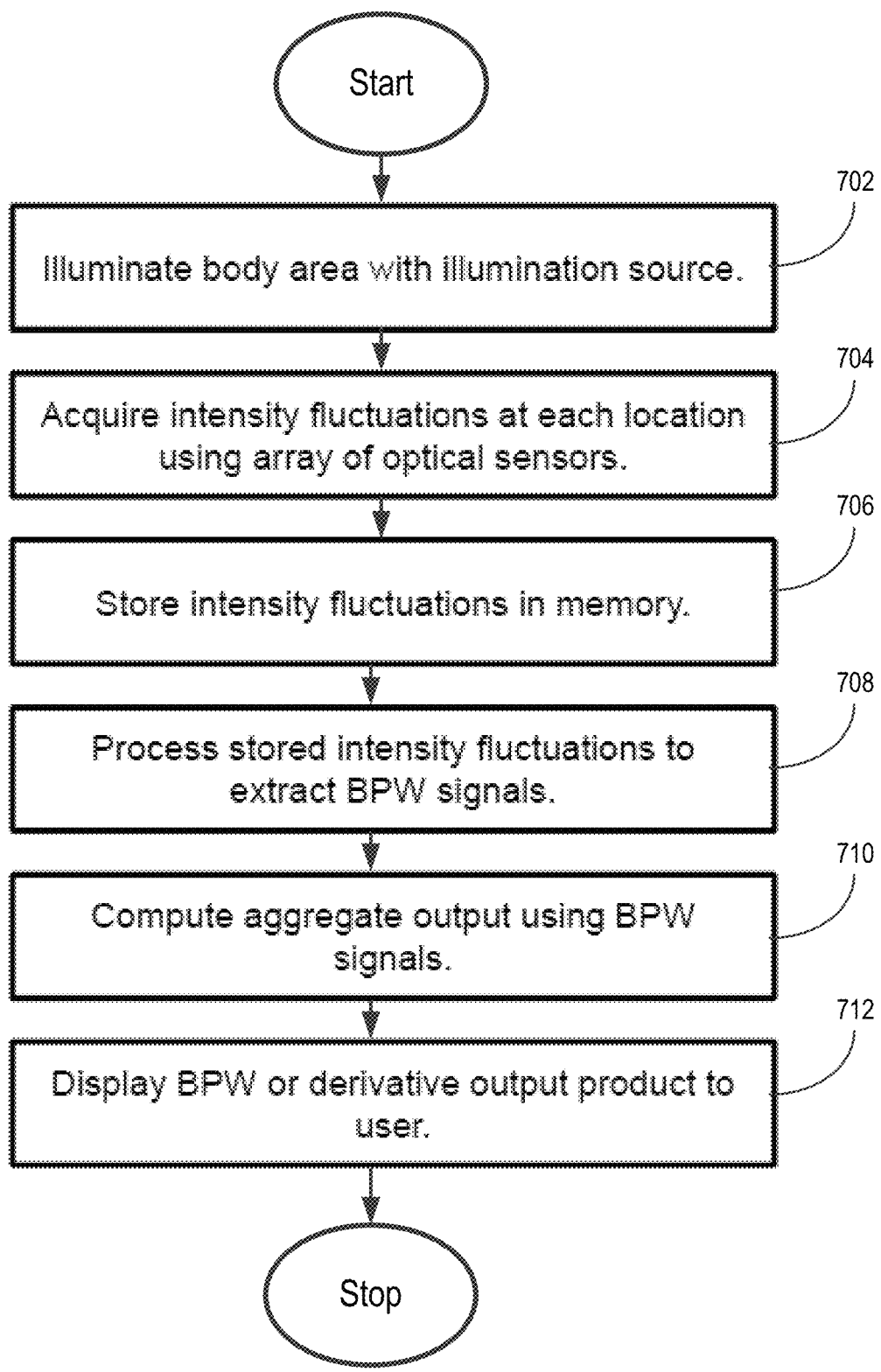
FIG. 7 shows an illustrative flow chart of a method in accordance with an embodiment.

Now referring to FIG. 7, shown is an illustrative flow chart of a method in accordance with an embodiment. The general phases include tissue illumination, illumination detection, BPW processing and extraction, aggregate output computation, and display visualization. For example, step 702 of the method involves illuminating a body area with a light source. Step 704 of the method is to collect intensity values at each location using an array of optical sensors (i.e., one or more virtual sensors). At step 706, the intensity fluctuations acquired by the sensors are transferred to the acquisition unit and stored in memory for further analysis. At step 708, one or more DSP techniques are applied to process these signals to extract the BPW signal from each suitable location, as explained above. At step 710, an aggregate output (e.g., parametric maps) is computed and, at step 712, displayed to the user for visualization.

Figure 8A:
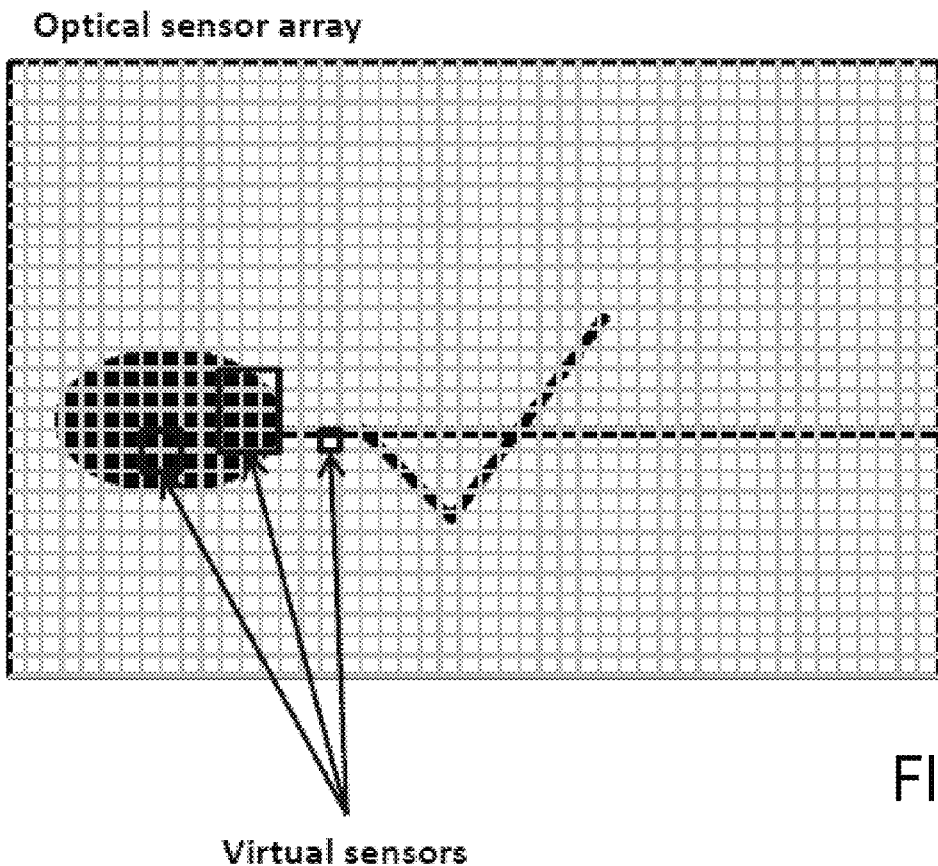
FIGS. 8A and 8B show the relationship between the optical sensors and virtual sensors in accordance with an illustrative embodiment.
Figure 8B:
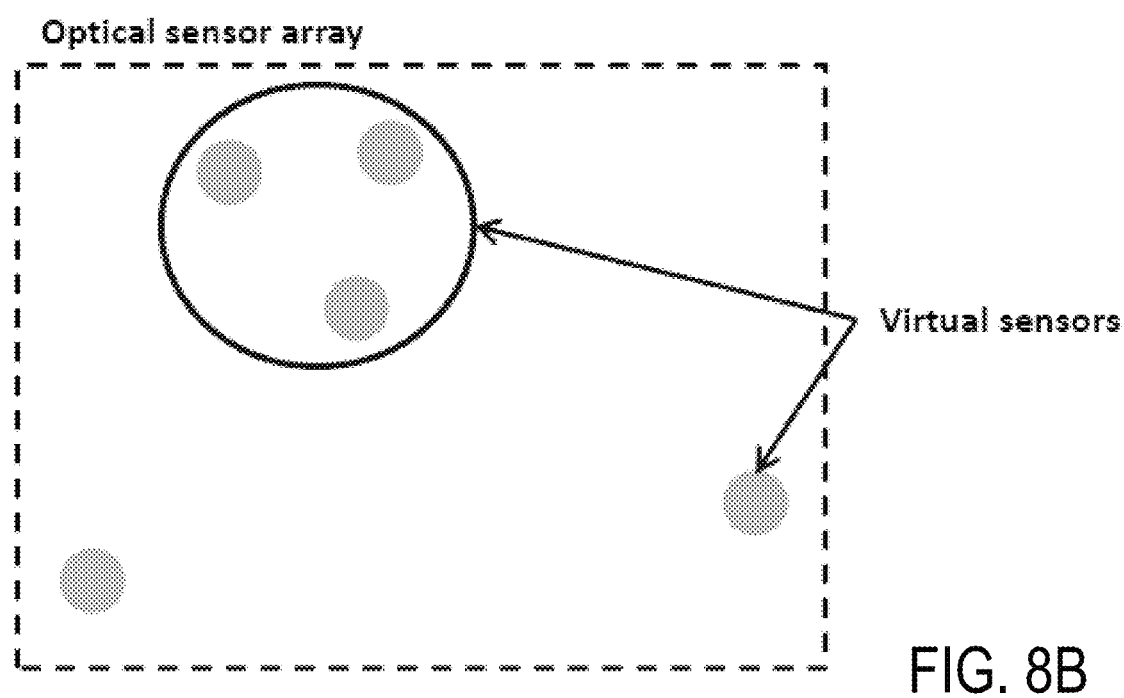

Now referring to FIGS. 8A and 8B, schematically shown is the relationship between an optical sensor array and virtual sensors. Virtual sensors are combinations of one or more optical sensors. Optical sensors may be, but are not limited to, a grid (e.g., CMOS, CCD, etc.), or a spatially distributed set of optical sensors (e.g. photodetectors, individual cameras, etc.).

Figure 9A:
FIGS. 9A-9C show a series of frames in which pulse visualization can be relayed to the user in accordance with an illustrative embodiment.
Figure 9B:
Figure 9C:
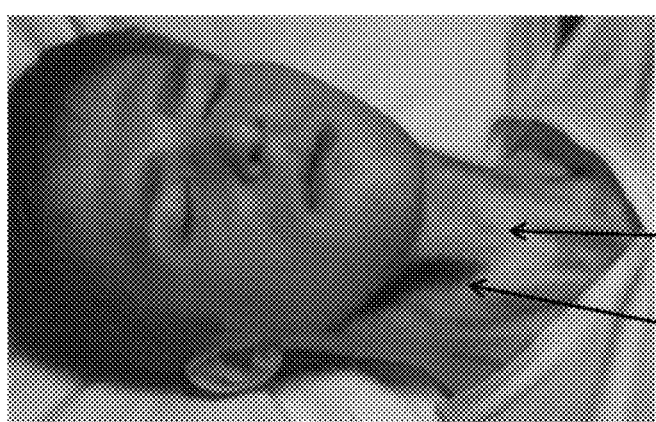

Now referring to FIGS. 9A-9C, shown are a series of frames in which pulse visualization can be relayed to the user. In this illustrative example, pixels are modified based on the BPW pulse, generating a video where the pulse at every location is made adaptively enhanced based on its strength. This visualization can be relayed visually using, for example, color maps and a video with changing pixel intensity values. These visual fluctuations are performed over the entire area synchronously with the BPW variation at that location. This enables visual analysis of pulses and blood flow. Mathematically:

$$\Omega = T(z)$$

where T is a transformation or mapping function that generates a normalized strength score $\Omega$ based on the BPW z, where $T(z):z \to [0,1]$. For example, T can follow a sigmoid definition:

$$T(z) = \frac{1}{1 + \exp(-a_1 \cdot SNR(z) + a_2)}$$

where $a_1$, $a_2$ are mapping parameters. Another example of T is:

$$T(z) = SNR(z) \cdot 1_{SNR(z) > \eta}$$

where 1 is the indicator function and $\eta$ is a threshold parameter. T(z) can use any other type of strength metric, for example RSSP, entropy, etc. It may be beneficial to apply a filter to reduce the "blockiness" of the video, for example a Gaussian low-pass filter:

$$\hat{\Omega} = \Omega * G(x),$$

$$G(x) = \frac{1}{\sqrt{2\pi\sigma^2}} \exp\left(-\frac{x^2}{2\sigma^2}\right)$$

Each location is then normalized to determine its amplified BPW:

$$\hat{\Omega}(x, y) = \frac{\hat{\Omega}(x, y) - \min(\hat{\Omega})}{\max(\hat{\Omega}) - \min(\hat{\Omega})} \in [0, 1]$$

These enhanced signals can be overlaid on top of the original frames for pulse visualization, for example, using a layer transparency. Various color maps can be applied for visualization, such as sequential and divergent color maps.

Figure 10:
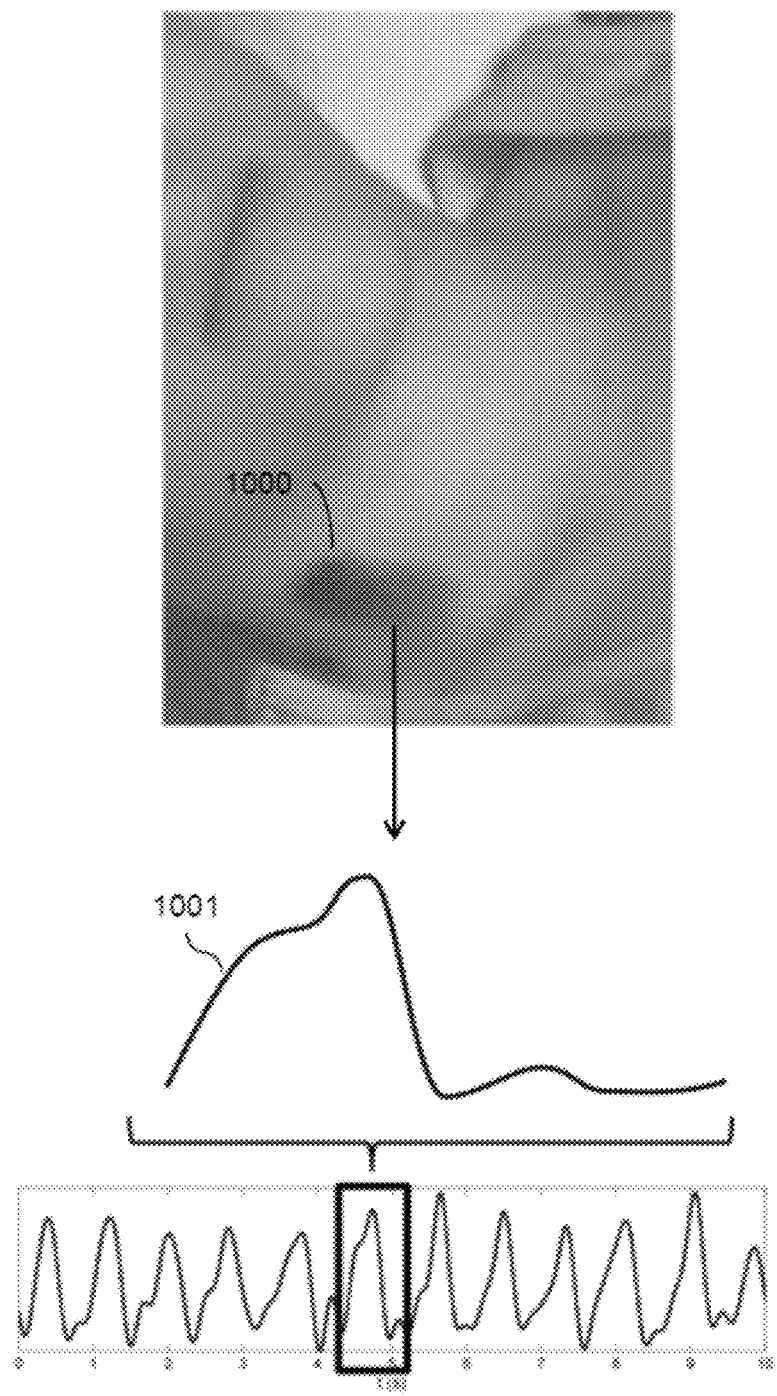
FIG. 10 shows an example of a pulsatile jugular venous pulse waveform extracted using the system.

The system and method is not constrained to analyzing arterial blood flow. During supine or reclined position, the pulsatile nature of the jugular vein (the "jugular venous pulse waveform" (JVP)) provides insight into cardiac function. Though this has been conventionally assessed using invasive catheterization, the system can provide an optical solution to this problem. Due to its direct link to the right atrium, differential heart pressure changes influence the jugular blood volume, which is analyzed by the proposed system. Specifically, the "inverted" nature of the pulse can be identified in direct or indirect means, possibly using the aforementioned parametric maps. FIG. 10 shows an example where the pulsatile characteristics of the jugular vein 1000 can be detected by the system and interpreted as the JVP 1001, with the characteristic JVP inflection points (a, c, x, v, and y waves) clearly observed. This information may be displayed to a doctor or primary caregiver for non-invasive JVP monitoring and diagnosis.

The system and method can extract BPWs without having direct view to the skin. For example, inspired from ballistocardiography, folds in the clothing fabric can be analyzed for heart beat-induced movements, elucidating the cardiac cycle. For example, the system can detect potential blood clots by observing changes in cardiovascular state, such as reduced flow (increased resistance), asymmetric flow, and pulse wave velocity analysis. For example, multi-individual tracking can be done to measure the cardiorespiratory parameters and BPWs of multiple individuals within the sensors' field of view. This has applications in both clinical monitoring and surveillance.

The system and method can be used for many different applications. For example, heart rate and respiratory rate can be extracted provide a personal cognitive stress indication, perhaps based on certain input stimuli. This can be abstracted to surveillance settings, where physiological patterns can be assessed for lie detection and detecting suspicious activity.

In one embodiment, the system and method can be used for vein visualization. Vein visualization is important for identifying veins for venous access procedures to reduce the number of stick attempts on patients, and may have applications in assessing increased central venous pressure with fluid accumulation. As opposed to arteries, veins generally have constant flow back to the heart, and do not exhibit pulsatility. Thus, locations with little-to-no pulsatility can be identified as venous structures.

In another embodiment of the system and method, infant cardiorespiratory monitoring can be accomplished by positioning the system above or beside the bed or crib. The system may extract BPWs, heart rate, respiratory rate, etc., and can transmit this data over a network so that the parents can monitor the infant's vital signs, or to caregivers in a neonatal intensive care unit (NICU). This monitoring is especially important for infants since conventional medical devices such as finger PPG, electrocardiagram, blood pressure cuffs are too large for the small anatomy of the infant, and may potentially damage the child's fragile skin. This type of monitoring can help prevent diseases that would otherwise need to be assessed clinically, such as infant death syndrome, and can monitor the health status of developing children.

In another embodiment, the system can be used for wound healing analysis, such as hematomas and burns. Generating parametric maps listed above can help identify areas that are healing, or track the healing process. Wound healing is often associated with vascular changes around the wound to facilitate the healing process. Vascular damage, such as hematomas, are caused by a rupture in the blood vessels. This leads to increase in blood volume and decrease in pulsatility. Assessing the change in pulsatility strength over time can help assess the effectiveness of healing.

In another embodiment, the system and method can be used to detect the direction of blood flow. This can be accomplished by analyzing time at which the pulse reaches a certain location, and track it over time. This can be helpful for generating blood vessel maps so that any changes in vascular structure over time can be tracked without the use of ionizing radiation, as in angiography or arteriography.

In another embodiment, the system and method can be used to detect the presence, absence or quality of BPWs in real-time to assess the effectiveness of cardiopulmonary resuscitation by relaying the effective carotid BPW through an aggregate output visualization. The quality and characteristics of the BPW can be used to estimate hemodynamic characteristics using a calibration model. If insufficient cerebral blood flow through the carotid artery is detected, a warning or alternative visualization can be sent to the user to alter their technique. The system can be operated in either fixed or handheld format using available embedded resources for real-time analysis.

In some embodiments, different types of optical BPW sensors can be used and fused together. For example, a temperature BPW sensor, such as a thermal camera, can be used to provide temperature information. This can help identify changes in temperatures over time, and for detecting and/or predicting illnesses before it is allowed to spread.

The system and method can be mounted in different indoor and outdoor locations. In some implementations, the system is mounted on a wall or ceiling, with a field of view encompassing a room or outdoor area. In another implementation, the system is mounted on a cart with wheels, for example a medical cart, which can be moved toward a user.

Figure 11:
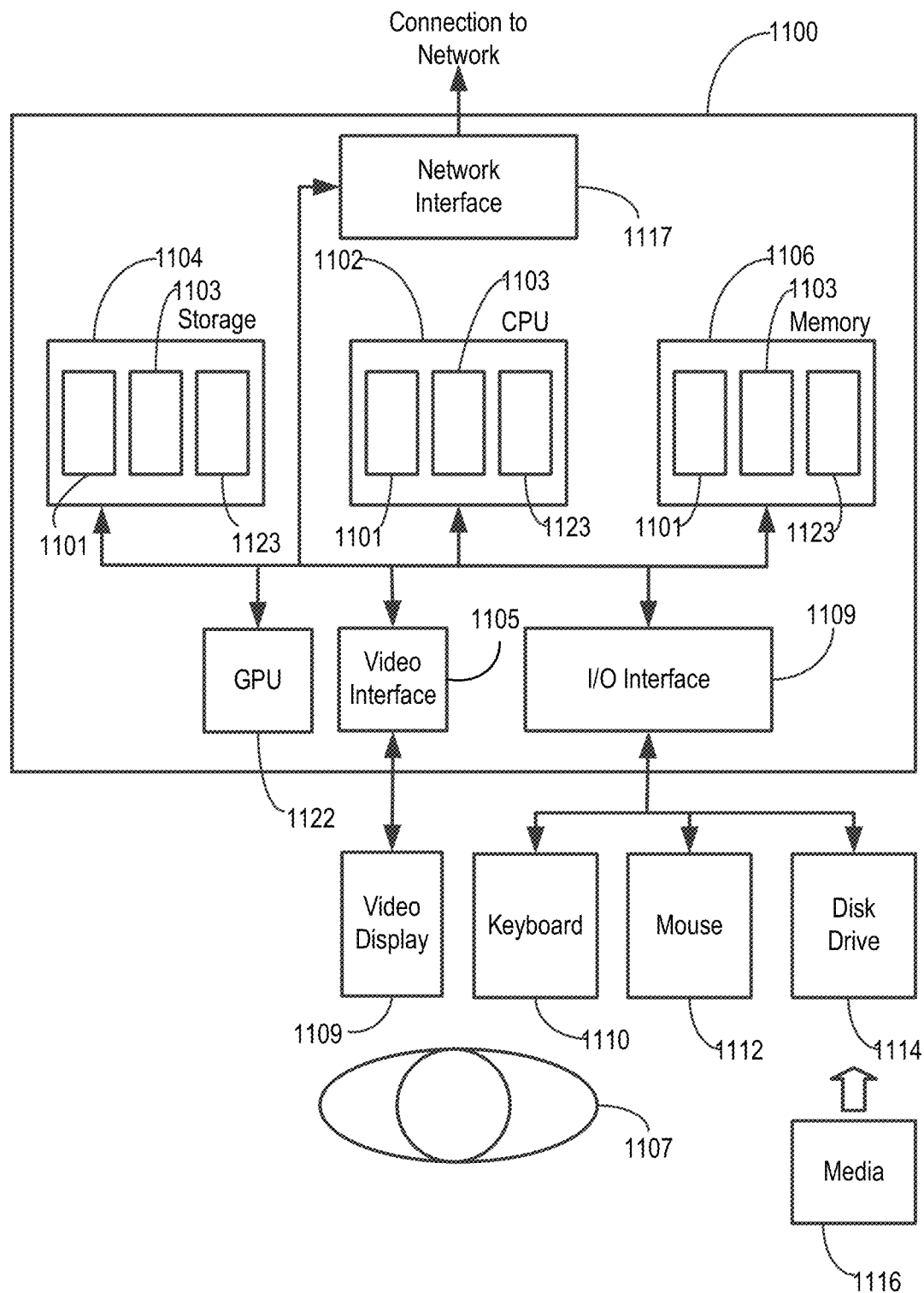
FIG. 11 shows a schematic block diagram of a generic computing device which may provide an operating environment for one or more embodiments.

Now referring to FIG. 11, shown is a suitably configured computer device, and associated communications networks, devices, software and firmware which may provide a platform for enabling one or more embodiments as described above. By way of example, FIG. 11 shows a generic computer device 1100 that may include a central processing unit ("CPU") 1102 connected to a storage unit 1104 and to a random access memory 1106. The CPU 1102 may process an operating system 1101, application program 1103, and data 1123. The operating system 1101, application program 1103, and data 1123 may be stored in storage unit 1104 and loaded into memory 1106, as may be required. Computer device 1100 may further include a graphics processing unit (GPU) 1122 which is operatively connected to CPU 1102 and to memory 1106 to offload intensive image processing calculations from CPU 1102 and run these calculations in parallel with CPU 1102. An operator 1110 may interact with the computer device 1100 using a video display 1108 connected by a video interface 1105, and various input/output devices such as a keyboard 1110, pointer 1112, and storage 1114 connected by an I/O interface 1109. In known manner, the pointer 1112 may be configured to control movement of a cursor or pointer icon in the video display 1108, and to operate various graphical user interface (GUI) controls appearing in the video display 1108. The computer device 1100 may form part of a network via a network interface 1111, allowing the computer device 1100 to communicate with other suitably configured data processing systems or circuits. One or more different types of sensors 1130 connected via a sensor interface 1132 may be used to search for and sense input from various sources. The sensors 1130 may be built directly into the generic computer device 1100, or optionally configured as an attachment or accessory to the generic computer device 1100.

Thus, in an aspect, there is provided a method of measuring arterial or venous blood pulse waveforms (BPWs) of a subject utilizing photoplethysmography (PPG), comprising: providing a plurality of virtual sensors positioned to cover a desired field-of-view of the subject, each virtual sensor adapted to detect and measure a BPW signal from an area of a subject's body and provide a BPW signal output; processing the BPW signal outputs of the plurality of virtual sensors to compare the BPWs at multiple areas of the subject's body to perform spatial perfusion analysis; and displaying at least one aggregate output based on the spatial perfusion analysis.

In an embodiment, the plurality of virtual sensors are formed from an array of one or more optical sensors positioned around the subject.

In another embodiment, the at least one aggregate output comprises a visualization of one or more perfusion patterns overlaid on an image of the subject.

In another embodiment, the at least one aggregate output further comprises aggregate statistics such as subject heart rate data and breathing rate data.

In another embodiment, the method further comprises using the signal of one of the virtual sensors as a reference waveform for cardiovascular monitoring in the generation of parametric maps for assessing BPW characteristics at various parts of the body simultaneously.

In another embodiment, the method further comprises the inclusion of a contact photoplethysmography (PPG) sensor which is connected to a digital signal processor and provides a reference BPW signal as a reference waveform.

In another embodiment, the method further comprises combining the BPW signal outputs of the plurality of virtual sensors with one or more reference signals to determine pulsality strength of a subject.

In another embodiment, the method further comprises monitoring the BPW signal outputs of the plurality of virtual sensors to determine the presence and quality of a BPW during cardiopulmonary resuscitation.

In another embodiment, the method further comprises using the presence and quality of a BPW to determine the effectiveness of cardiopulmonary resuscitation.

In another embodiment, the method further comprises displaying an aggregate visualization to describe the effectiveness of cardiopulmonary resuscitation.

In another embodiment, the method further comprises utilizing the BPW signal outputs of the plurality of virtual sensors to monitor a jugular venous pulse waveform (JVP) of a subject.

In another embodiment, the method further comprises utilizing the BPW signal outputs of the plurality of virtual sensors to monitor neonates in naturalistic or intensive care environments.

In another aspect, there is provided a system for measuring arterial or venous blood pulse waveforms (BPWs) of a subject utilizing photoplethysmography (PPG), comprising: a plurality of virtual sensors positioned to cover a desired field-of-view of the subject, each virtual sensor adapted to detect and measure a BPW signal from an area of a subject's body and provide a BPW signal output; a processor for processing the BPW signal outputs of the plurality of virtual sensors to compare the BPWs at multiple areas of the subject's body to perform spatial perfusion analysis; and a display for displaying at least one aggregate output based on the spatial perfusion analysis.

In an embodiment, the plurality of virtual sensors are formed from an array of one or more optical sensors positioned around the subject.

In another embodiment, the at least one aggregate output comprises a visualization of one or more perfusion patterns overlaid on an image of the subject.

In another embodiment, the at least one aggregate output further comprises aggregate statistics such as subject heart rate data and breathing rate data.

In another embodiment, the system is further adapted to use the signal of one of the virtual sensors as a reference waveform for cardiovascular monitoring in the generation of parametric maps for assessing BPW characteristics at various parts of the body simultaneously.

In another embodiment, the system further comprises the inclusion of a contact photoplethysmography (PPG) sensor which is connected to a digital signal processor and provides a reference BPW signal as a reference waveform.

In another embodiment, the system is further adapted to combine the BPW signal outputs of the plurality of virtual sensors with one or more reference signals to determine pulsality strength of a subject.

In another embodiment, the system is further adapted to monitor the BPW signal outputs of the plurality of virtual sensors to determine the presence and quality of a BPW during cardiopulmonary resuscitation.

In another embodiment, the presence and quality of a BPW is used to determine the effectiveness of cardiopulmonary resuscitation.

In another embodiment, the system is further adapted to display an aggregate visualization to describe the effectiveness of cardiopulmonary resuscitation.

In another embodiment, the system is further adapted to utilize the BPW signal outputs of the plurality of virtual sensors to monitor a jugular venous pulse waveform (JVP) of a subject.

In another embodiment, the system is further adapted to utilize BPW signal outputs of the plurality of virtual sensors to monitor neonates in naturalistic or intensive care environments.

While illustrative embodiments have been described above by way of example, it will be appreciated that various changes and modifications may be made without departing from the scope of the system and method, which is defined by the following claims.

REFERENCES

[1] J. Allen, "Photoplethysmography and its application in clinical physiological measurement," *Physiological Measurement*, vol. 28, no. 3, pp. R1-R39, 2007.

[2] M. Hulsbusch and V. Blazek, "Contactless mapping of rhythmical phenomena in tissue perfusion using PPGI," in *Proc SPIE* 4683, 2002.

[3] F. Wieringa, F. Mastik and A. Van der Steen, "Contactless multiple wavelength photoplethysmographic imaging: a first step toward "SpO2 camera" technology," *Annals of Biomedical Engineering*, vol. 33, no. 8, pp. 1034-1041, 2005.

[4] K. Humphreys, T. Ward and C. Markham, "Noncontact simultaneous dual wavelength photoplethysmography: a further step toward noncontact pulse oximetry," *Review of Scientific Instruments*, vol. 78, no. 4, p. 044304, 2007.

[5] G. Cennini, J. Arguel, K. Aksit and A. van Leest, "Heart rate monitoring via remote photoplethysmography with motion artifacts reduction," *Optics Express*, vol. 18, no. 5, pp. 4867-4875, 2010.

[6] W. Verkruysse, L. O. Svaasand and J. S. Nelson, "Remote plethysmographic imaging using ambient light," *Optics Express*, vol. 16, no. 26, pp. 2143-21445, 2008.

[7] Y. Sun, S. Hu, V. Azorin-Peris, S. Greenwald, J. Chambers and Y. Zhu, "Motion-compensated noncontact imaging photoplethysmography to monitor cardiorespiratory status during exercise," *Journal of Biomedical Optics*, vol. 16, no. 7, pp. 0770101-0770109, 2011.

[8] S. Xu, L. Sun and G. K. Rohde, "Robust efficient estimation of heart rate pulse from video," *Biomedical Optics Express*, vol. 5, no. 4, pp. 1124-1135, 2014.

[9] L. A. A. Verkruysse, V. Jeanne, J. P. Cleary, C. Lieber, J. S. Nelson and S. Bambang Oetomo, "Non-contact heart rate monitoring utilizing camera photoplethysmography in the neonatal intensive care unit—A pilot study," *Early Human Development*, vol. 89, no. 12, pp. 943-948, 2013.

[10] M.-Z. Poh, D. J. McDuff and R. W. Picard, "Non-contact, automated cardiac pulse measurements using video imaging and blind source separation," *Optics Express*, vol. 18, no. 10, pp. 10762-10774, 2010.

[11] J. Zheng, S. Hu, V. Azorin-Peris, A. Echiadis, V. Chouliaras and R. Summers, "Remote simultaneous dual wavelength imaging photoplethysmography: a further step towards 3-D mapping of skin blood microcirculation," in *Proc SPIE* 6850, 2008.

[12] A. A. K. Nippolainen, S. Miridonov, V. Teplov, R. Saarenheimo and Ervin, "Photoplethysmographic imaging of high spatial resolution," *Biomedical Optics Express*, vol. 2, no. 4, pp. 996-1006, 2011.

[13] M. P. Tarvainen, P. O. Ranta-Aho and P. A. Karjalainen, "An advanced detrending method with application to HRV analysis," *IEEE Transactions on Biomedical Engineering*, vol. 49, no. 2, pp. 172-175, 2002.

[14] D. McDuff, R. Picard and S. Gontarek, "Methods and Apparatus for Physiological Measurement Using Color Band Photoplethysmographic Sensor". U.S. Pat. No. 6,778,698 Oct. 2015.

[15] Survi, K. Y. A. L., and Lalit Keshav Mestha. "Cardiac pulse rate estimation from source video data." U.S. Pat. No. 9,336,594. 10 May 2016.

The invention claimed is:

1. A method of measuring arterial and venous blood pulse waveforms (BPWs) of a subject utilizing spatially selective lighting changes, comprising:
providing a plurality of virtual sensors positioned to cover a desired field-of-view of the subject, each virtual sensor adapted to detect and measure intensity of arterial and venous BPW signals from an area of a subject's body and provide arterial and venous BPW signal outputs using spatially coded lighting and sensing;
processing the arterial and venous BPW signal outputs of the plurality of virtual sensors to compare the arterial and venous BPWs at multiple areas of the subject's body in the time and frequency domain to perform spatial perfusion analysis; and
displaying at least one arterial and venous pulsatility perfusion aggregate output utilizing different colors to show the intensity of arterial and venous BPWs.

2. The method of claim 1, wherein the plurality of virtual sensors are formed from an array of one or more optical sensors positioned around the subject.

3. The method of claim 1, wherein the at least one aggregate output comprises a visualization of one or more perfusion patterns overlaid on an image of the subject.

4. The method of claim 3, wherein the at least one aggregate output further comprises aggregate statistics such as subject heart rate data and breathing rate data.

5. The method of claim 1, further comprising using the signal of one of the virtual sensors as a reference waveform for cardiovascular monitoring in the generation of parametric maps for assessing BPW characteristics at various parts of the body simultaneously.

6. The method of claim 1, further comprising the inclusion of a contact photoplethysmography (PPG) sensor which is connected to a digital signal processor and provides reference arterial and venous BPW signals as reference waveforms for pulsatility strength analysis.

7. The method of claim 1, further comprising combining the arterial and venous BPW signal outputs of the plurality of virtual sensors with one or more reference signals to determine pulsality strength of a subject.

8. The method of claim 1, further comprising monitoring the arterial and venous BPW signal outputs of the plurality of virtual sensors to determine the presence and quality of a BPW during mechanical cardiopulmonary resuscitation.

9. The method of claim 8, further comprising using the presence and quality of a BPW to determine the effectiveness of cardiopulmonary resuscitation.

10. The method of claim 9, further comprising displaying an aggregate visualization to describe the effectiveness of cardiopulmonary resuscitation.

11. The method of claim 1, further comprising utilizing the arterial and venous BPW signal outputs of the plurality of virtual sensors to monitor neonates innaturalistic or intensive care environments.

12. A system for measuring arterial and venous blood pulse waveforms (BPWs) of a subject utilizing spatially selective lighting changes, comprising:
   a plurality of virtual sensors positioned to cover a desired field-of-view of the subject, each virtual sensor adapted to detect and measure intensity of arterial and venous BPW signals from an area of a subject's body and provide arterial and venous BPW signal outputs using spatially coded lighting and sensing;
   a processor for processing the BPW signal outputs of the plurality of virtual sensors to compare the BPWs at multiple areas of the subject's body to perform spatial perfusion analysis; and
   a display for displaying at least one arterial and venous pulsality perfusion aggregate output based on the spatial perfusion analysis utilizing different colors to show the intensity of arterial and venous BPWs.

13. The system of claim 12, wherein the plurality of virtual sensors are formed from an array of one or more optical sensors positioned around the subject.

14. The system of claim 12, wherein the at least one aggregate output comprises a visualization of one or more perfusion patterns overlaid on an image of the subject.

15. The system of claim 14, wherein the at least one aggregate output further comprises aggregate statistics such as subject heart rate data and breathing rate data.

16. The system of claim 12, wherein the system is further adapted to use the signal of one of the virtual sensors as a reference waveform for cardiovascular monitoring in the generation of parametric maps for assessing BPW characteristics at various parts of the body simultaneously.

17. The system of claim 12, further comprising the inclusion of a contact photoplethysmography (PPG) sensor which is connected to a digital signal processor and provides reference BPW signals as reference waveforms.

18. The system of claim 12, wherein the system is further adapted to combine the arterial and venous BPW signal outputs of the plurality of virtual sensors with one or more reference signals to determine pulsality strength of a subject.

19. The system of claim 12, wherein the system is further adapted to monitor the arterial and venous BPW signal outputs of the plurality of virtual sensors to determine the presence and quality of a BPW during cardiopulmonary resuscitation.

20. The system of claim 19, wherein the presence and quality of a BPW is used to determine the effectiveness of cardiopulmonary resuscitation.

21. The system of claim 20, wherein the system is further adapted to display an aggregate visualization to describe the effectiveness of cardiopulmonary resuscitation.

22. The system of claim 12, wherein the system is further adapted to utilize the arterial and venous BPW signal outputs of the plurality of virtual sensors to monitor neonates in naturalistic or intensive care environments.

23. A method of measuring arterial and venous blood pulse waveforms (BPWs) of a subject utilizing photoplethysmography (PPG), comprising:
   providing a plurality of virtual sensors positioned to cover a desired field-of-view of the subject, each virtual sensor adapted to detect and measure a BPW signal from an area of a subject's body and provide a BPW signal output;
   processing the BPW signal outputs of the plurality of virtual sensors to compare the BPWs at multiple areas of the subject's body to perform spatial perfusion analysis;
   utilizing the BPW signal outputs of the plurality of virtual sensors to monitor a jugular venous pulse waveform (JVP) of a subject; and
   displaying at least one aggregate output based on the spatial perfusion analysis.

24. A system for measuring arterial and venous blood pulse waveforms (BPWs) of a subject utilizing photoplethysmography (PPG), comprising:
   a plurality of virtual sensors positioned to cover a desired field-of-view of the subject, each virtual sensor adapted to detect and measure a BPW signal from an area of a subject's body and provide a BPW signal output;
   a processor for processing the BPW signal outputs of the plurality of virtual sensors to compare the BPWs at multiple areas of the subject's body to perform spatial perfusion analysis; and
   a display for displaying at least one aggregate output based on the spatial perfusion analysis;
   wherein the system is adapted to utilize the BPW signal outputs of the plurality of virtual sensors to monitor a jugular venous pulse waveform (JVP) of a subject.

* * * * *